(12) United States Patent
Mermuys et al.

(10) Patent No.: US 10,869,767 B2
(45) Date of Patent: *Dec. 22, 2020

(54) INTERVERTEBRAL IMPLANT

(71) Applicant: Pioneer Surgical Technology, Inc., Marquette, MI (US)

(72) Inventors: Daniel Ryan Mermuys, Marquette, MI (US); Scott J. Perrow, Ishpeming, MI (US); Steven A. Schopler, Bakersfield, CA (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 8 days.

This patent is subject to a terminal disclaimer.

(21) Appl. No.: 16/228,858

(22) Filed: Dec. 21, 2018

(65) Prior Publication Data

US 2019/0125544 A1    May 2, 2019

Related U.S. Application Data

(63) Continuation of application No. 15/886,164, filed on Feb. 1, 2018, now Pat. No. 10,182,920, which is a (Continued)

(51) Int. Cl.
*A61F 2/44* (2006.01)
*A61F 2/46* (2006.01)
(Continued)

(52) U.S. Cl.
CPC .............. *A61F 2/442* (2013.01); *A61F 2/447* (2013.01); *A61F 2/4611* (2013.01);
(Continued)

(58) Field of Classification Search
CPC ...... A61F 2/30767; A61F 2/44; A61F 2/4475; A61F 2/46; A61F 2/4611;
(Continued)

(56) References Cited

U.S. PATENT DOCUMENTS 3,707,107 A    12/1972  Bieri
4,349,921 A     9/1982  Kuntz
(Continued)

FOREIGN PATENT DOCUMENTS

DE    10309702    9/2004
EP     1138285   10/2001
(Continued)

OTHER PUBLICATIONS

Medtronic Sofamor Danek, Union/Union L, Anterior & Lateral Impacted Fusion Devices, Clear Choice of Stabilization, 2001, (25 pages).

*Primary Examiner* — Anu Ramana
(74) *Attorney, Agent, or Firm* — Fitch, Even, Tabin & Flannery LLP

(57) ABSTRACT

An intervertebral implant for being implanted between adjacent vertebrae is provided. The implant includes a generally elongate implant body having a length extending between opposite longitudinal ends thereof, a superior face and an inferior face. The superior face and inferior face include cortical teeth adjacent to the implant body longitudinal ends. Additionally, the superior and inferior faces include longitudinally central teeth intermediate the cortical teeth and have bone engaging ends. The central teeth have a sharper configuration than that of the cortical teeth bone engaging ends for biting into the softer central bone material of the vertebrae. The cortical teeth are arranged in a first density per unit area and the central teeth are arranged in a second density per unit area that is less than the first density.

11 Claims, 10 Drawing Sheets

Related U.S. Application Data continuation of application No. 15/176,707, filed on Jun. 8, 2016, now Pat. No. 9,883,949, which is a continuation of application No. 14/734,764, filed on Jun. 9, 2015, now Pat. No. 9,387,092, which is a continuation of application No. 13/648,086, filed on Oct. 9, 2012, now Pat. No. 9,132,021.

(60) Provisional application No. 61/545,030, filed on Oct. 7, 2011.

(51) Int. Cl.
*A61F 2/30* (2006.01)
*A61F 2/28* (2006.01)

(52) U.S. Cl.
CPC ......... *A61F 2/3094* (2013.01); *A61F 2/30965* (2013.01); *A61F 2002/2835* (2013.01); *A61F 2002/30006* (2013.01); *A61F 2002/3008* (2013.01); *A61F 2002/3082* (2013.01); *A61F 2002/3084* (2013.01); *A61F 2002/30092* (2013.01); *A61F 2002/30182* (2013.01); *A61F 2002/30593* (2013.01); *A61F 2002/30774* (2013.01); *A61F 2002/30785* (2013.01); *A61F 2002/30822* (2013.01); *A61F 2002/30827* (2013.01); *A61F 2002/30828* (2013.01); *A61F 2002/30836* (2013.01); *A61F 2002/30841* (2013.01); *A61F 2002/30843* (2013.01); *A61F 2002/30881* (2013.01); *A61F 2002/30892* (2013.01); *A61F 2002/30904* (2013.01); *A61F 2002/30978* (2013.01); *A61F 2002/4627* (2013.01); *A61F 2002/4629* (2013.01); *A61F 2220/0016* (2013.01); *A61F 2230/0082* (2013.01); *A61F 2310/00017* (2013.01); *A61F 2310/00023* (2013.01); *A61F 2310/00221* (2013.01); *A61F 2310/00293* (2013.01); *A61F 2310/00592* (2013.01); *A61F 2310/00796* (2013.01)

(58) Field of Classification Search
CPC .. A61F 2002/30841; A61F 2002/30843; A61F 2002/30845; A61F 2002/30774; A61F 2002/30797

See application file for complete search history.

(56) References Cited

U.S. PATENT DOCUMENTS

| | | |
|---|---|---|
| 4,799,372 A | 1/1989 | Marcon |
| 4,834,757 A | 5/1989 | Brantigan |
| 5,314,477 A | 5/1994 | Marnay |
| 5,370,697 A | 12/1994 | Baumgartner |
| 5,474,558 A | 12/1995 | Neubardt |
| 5,609,635 A | 3/1997 | Michelson |
| 5,614,205 A | 3/1997 | Usala |
| 5,766,252 A | 6/1998 | Henry |
| 5,772,661 A | 6/1998 | Michelson |
| 5,776,198 A | 7/1998 | Rabbe |
| 5,776,199 A | 7/1998 | Michelson |
| 5,797,909 A | 8/1998 | Michelson |
| 5,824,331 A | 10/1998 | Usala |
| 5,865,845 A | 2/1999 | Thalgott |
| 5,888,227 A | 5/1999 | Cottle |
| 5,922,339 A | 7/1999 | Usala |
| 6,013,591 A | 1/2000 | Ying |
| 6,068,974 A | 5/2000 | Klann |
| 6,132,465 A | 10/2000 | Ray |
| 6,231,881 B1 | 5/2001 | Usala |
| 6,261,587 B1 | 7/2001 | Usala |
| 6,270,977 B1 | 8/2001 | Klann |
| 6,277,149 B1 | 8/2001 | Boyle |
| 6,315,994 B2 | 11/2001 | Usala |
| 6,352,707 B1 | 3/2002 | Usala |
| 6,458,159 B1 | 10/2002 | Thalgott |
| 6,478,823 B1 | 11/2002 | Michelson |
| 6,482,233 B1 | 11/2002 | Aebi |
| 6,520,993 B2 | 2/2003 | James |
| 6,530,955 B2 | 3/2003 | Boyle |
| 6,582,453 B1 | 6/2003 | Tran |
| 6,676,703 B2 | 1/2004 | Biscup |
| 6,713,079 B2 | 3/2004 | Usala |
| 6,719,794 B2 | 4/2004 | Gerber |
| 6,730,315 B2 | 5/2004 | Usala |
| 6,733,535 B2 | 5/2004 | Michelson |
| 6,746,484 B1 | 6/2004 | Liu |
| 6,790,455 B2 | 9/2004 | Chu |
| 6,827,740 B1 | 12/2004 | Michelson |
| 6,843,805 B2 | 1/2005 | Webb |
| 6,872,208 B1 | 3/2005 | McBride |
| 6,890,355 B2 | 5/2005 | Michelson |
| 6,964,687 B1 | 11/2005 | Bernard |
| 6,974,480 B2 | 12/2005 | Messerli |
| 6,979,353 B2 | 12/2005 | Bresina |
| 6,991,654 B2 | 1/2006 | Foley |
| 7,018,416 B2 | 3/2006 | Hanson |
| 7,041,137 B2 | 5/2006 | Fulton |
| 7,044,972 B2 | 5/2006 | Mathys, Jr. |
| 7,063,725 B2 | 6/2006 | Foley |
| RE39,196 E | 7/2006 | Ying |
| 7,125,425 B2 | 10/2006 | Foley |
| 7,137,997 B2 | 11/2006 | Paul |
| 7,217,293 B2 | 5/2007 | Branch, Jr. |
| 7,303,583 B1 | 12/2007 | Schar |
| 7,309,358 B2 | 12/2007 | Berry |
| 7,326,251 B2 | 2/2008 | McCombe |
| 7,455,692 B2 | 11/2008 | Michelson |
| 7,479,160 B2 | 1/2009 | Branch |
| 7,641,690 B2 | 1/2010 | Abdou |
| 7,662,186 B2 | 2/2010 | Bagga |
| 7,763,078 B2 | 7/2010 | Peterman |
| 7,776,095 B2 | 8/2010 | Peterman |
| 7,824,427 B2 | 11/2010 | Perez-Cruet |
| 7,846,210 B2 | 12/2010 | Perez-Cruet |
| 7,850,736 B2 | 12/2010 | Heinz |
| 7,875,080 B2 | 1/2011 | Puno |
| 7,901,458 B2 | 3/2011 | DeRidder |
| 7,918,891 B1 | 4/2011 | Curran |
| 7,951,203 B2 | 5/2011 | McCombe |
| 7,988,734 B2 | 8/2011 | Peterman |
| 8,002,837 B2 | 8/2011 | Stream |
| 8,083,799 B2 | 12/2011 | Baynham |
| 8,137,402 B2 | 3/2012 | Eckman |
| 8,142,508 B1 | 3/2012 | Bruffey |
| 8,172,905 B2 | 5/2012 | Baynham |
| 8,187,334 B2 | 5/2012 | Curran |
| 8,192,356 B2 | 6/2012 | Miles |
| 8,192,357 B2 | 6/2012 | Miles |
| 8,216,316 B2 | 7/2012 | Kirschman |
| 8,241,359 B2 | 8/2012 | Davis |
| 8,262,737 B2 | 9/2012 | Bagga |
| 8,308,805 B2 | 11/2012 | Lynn |
| 8,343,224 B2 | 1/2013 | Lynn |
| 8,361,156 B2 | 1/2013 | Curran |
| 8,700,198 B2 | 4/2014 | Conway |
| 9,132,021 B2 | 9/2015 | Mermuys |
| 9,387,092 B2 | 7/2016 | Mermuys |
| 9,883,949 B2 | 2/2018 | Mermuys |
| 10,182,920 B2 | 1/2019 | Mermuys |
| 2001/0047208 A1 | 11/2001 | Michelson |
| 2001/0049560 A1 | 12/2001 | Paul |
| 2002/0013624 A1 | 1/2002 | Michelson |
| 2002/0087212 A1 | 7/2002 | James |
| 2002/0091390 A1 | 7/2002 | Michelson |
| 2002/0151894 A1 | 10/2002 | Melkent |
| 2003/0040798 A1 | 2/2003 | Michelson |
| 2003/0083748 A1 | 5/2003 | Lee |
| 2003/0135275 A1 | 7/2003 | Garcia |
| 2003/0135279 A1 | 7/2003 | Michelson |
| 2003/0139812 A1 | 7/2003 | Garcia |
| 2003/0181981 A1 | 9/2003 | Lemaire |

(56) References Cited

U.S. PATENT DOCUMENTS

| | | |
|---|---|---|
| 2004/0082999 A1 | 4/2004 | Mathys |
| 2004/0117018 A1 | 6/2004 | Michelson |
| 2004/0127993 A1 | 7/2004 | Kast |
| 2004/0127994 A1 | 7/2004 | Kast |
| 2005/0031704 A1 | 2/2005 | Ahn |
| 2005/0049589 A1 | 3/2005 | Jackson |
| 2005/0071005 A1 | 3/2005 | Carli |
| 2005/0118230 A1 | 6/2005 | Hill |
| 2005/0143820 A1 | 6/2005 | Zucherman |
| 2005/0143822 A1 | 6/2005 | Paul |
| 2006/0167549 A1 | 7/2006 | Mathys, Jr. |
| 2006/0217807 A1 | 9/2006 | Peterman |
| 2007/0027544 A1 | 2/2007 | McCord |
| 2007/0162138 A1 | 7/2007 | Heinz |
| 2007/0293948 A1 | 12/2007 | Bagga |
| 2007/0293949 A1 | 12/2007 | Salemi |
| 2008/0009945 A1 | 1/2008 | Pacheco |
| 2008/0065219 A1 | 3/2008 | Dye |
| 2008/0154377 A1 | 6/2008 | Voellmicke |
| 2008/0188940 A1 | 8/2008 | Cohen |
| 2008/0195209 A1 | 8/2008 | Garcia |
| 2008/0200985 A1 | 8/2008 | Robie |
| 2008/0208342 A1 | 8/2008 | Hanson |
| 2008/0221695 A1 | 9/2008 | Jacofsky |
| 2008/0234828 A1 | 9/2008 | Wagner |
| 2008/0243252 A1 | 10/2008 | Hansen |
| 2008/0288076 A1 | 11/2008 | Soo |
| 2008/0306598 A1 | 12/2008 | Hansen |
| 2009/0030519 A1 | 1/2009 | Falahee |
| 2009/0062917 A1 | 3/2009 | Foley |
| 2009/0105824 A1 | 4/2009 | Jones |
| 2009/0105825 A1 | 4/2009 | Foreman |
| 2009/0248163 A1 | 10/2009 | King |
| 2009/0276049 A1 | 11/2009 | Weiland |
| 2009/0299479 A1 | 12/2009 | Jones |
| 2010/0070039 A1 | 3/2010 | Guyer |
| 2010/0076559 A1 | 3/2010 | Bagga |
| 2010/0171306 A1 | 7/2010 | Gillot |
| 2010/0191337 A1 | 7/2010 | Zamani |
| 2010/0204798 A1 | 8/2010 | Gerbec |
| 2010/0228296 A1 | 9/2010 | Vraney |
| 2011/0045087 A1 | 2/2011 | Kerr |
| 2011/0093078 A1 | 4/2011 | Puno |
| 2011/0106259 A1 | 5/2011 | Lindenmann |
| 2011/0112642 A1 | 5/2011 | Tohmeh |
| 2011/0208309 A1 | 8/2011 | Peterson |
| 2011/0245923 A1 | 10/2011 | Cobb |
| 2011/0251689 A1 | 10/2011 | Seifert |
| 2011/0264218 A1 | 10/2011 | Asaad |
| 2011/0270402 A1 | 11/2011 | Frey |
| 2011/0282454 A1 | 11/2011 | Ullrich |
| 2011/0295372 A1 | 12/2011 | Peterman |
| 2011/0301710 A1 | 12/2011 | Mather |
| 2011/0313531 A1 | 12/2011 | Lechmann |
| 2011/0319998 A1 | 12/2011 | ONeil |
| 2011/0320000 A1 | 12/2011 | ONeil |
| 2012/0010715 A1 | 1/2012 | Spann |
| 2012/0010717 A1 | 1/2012 | Spann |
| 2012/0029641 A1 | 2/2012 | Curran |
| 2012/0035730 A1 | 2/2012 | Spann |
| 2012/0071984 A1 | 3/2012 | Michelson |
| 2012/0083885 A1 | 4/2012 | Thibodeau |
| 2012/0130494 A1 | 5/2012 | DeLurio |
| 2012/0158144 A1 | 6/2012 | Ullrich |
| 2012/0179261 A1 | 7/2012 | Soo |
| 2012/0232664 A1 | 9/2012 | Ulrich |
| 2012/0239150 A1 | 9/2012 | Ullrich |
| 2012/0239151 A1 | 9/2012 | Ulrich |
| 2012/0239152 A1 | 9/2012 | Ullrich |
| 2012/0239153 A1 | 9/2012 | Ullrich |
| 2012/0239154 A1 | 9/2012 | Ullrich |
| 2012/0245694 A1 | 9/2012 | Ullrich |
| 2012/0265306 A1 | 10/2012 | Trieu |
| 2012/0265307 A1 | 10/2012 | Guyer |
| 2012/0265311 A1 | 10/2012 | Mather |
| 2012/0277869 A1 | 11/2012 | Siccardi |
| 2012/0277870 A1 | 11/2012 | Wolters |
| 2012/0277876 A1 | 11/2012 | Ullrich |
| 2012/0283834 A1 | 11/2012 | Gottlieb |
| 2012/0283838 A1 | 11/2012 | Rhoda |
| 2012/0290091 A1 | 11/2012 | Kirschman |
| 2012/0303123 A1 | 11/2012 | Robie |
| 2012/0303127 A1 | 11/2012 | Ullrich |
| 2012/0303128 A1 | 11/2012 | Ullrich |
| 2012/0303129 A1 | 11/2012 | Bagga |
| 2012/0310354 A1 | 12/2012 | Ullrich |
| 2012/0316650 A1 | 12/2012 | Ullrich |
| 2012/0316653 A1 | 12/2012 | Ullrich |
| 2013/0006363 A1 | 1/2013 | Ullrich |
| 2013/0018466 A1 | 1/2013 | Yu |
| 2013/0030534 A1 | 1/2013 | DeLurio |

FOREIGN PATENT DOCUMENTS

| | | |
|---|---|---|
| EP | 1698305 | 9/2006 |
| EP | 2085056 | 8/2009 |
| FR | 2827157 | 1/2003 |
| JP | 2000210316 | 8/2000 |
| WO | 0038574 | 7/2000 |
| WO | 0137728 | 5/2001 |
| WO | 200238086 | 5/2002 |
| WO | 03005887 | 1/2003 |
| WO | 2005077307 | 8/2005 |
| WO | 2011056172 | 5/2011 |
| WO | 2011097905 | 8/2011 |
| WO | 2012008279 | 1/2012 |
| WO | 2012010327 | 1/2012 |
| WO | 2013008111 | 1/2013 |

INTERVERTEBRAL IMPLANT

CROSS-REFERENCE TO RELATED APPLICATION

This application is a continuation of prior application Ser. No. 15/886,164, filed Feb. 1, 2018, which is a continuation of prior application Ser. No. 15/176,707, filed Jun. 8, 2016, now U.S. Pat. No. 9,883,949, issued Feb. 6, 2018, which is a continuation of prior application Ser. No. 14/734,764, filed Jun. 9, 2015, now U.S. Pat. No. 9,387,092, issued Jul. 12, 2016, which is a continuation of prior application Ser. No. 13/648,086, filed Oct. 9, 2012, now U.S. Pat. No. 9,132,021, issued Sep. 15, 2015, which claims benefit of U.S. Provisional Application No. 61/545,030, filed Oct. 7, 2011, which are hereby incorporated herein by reference in their entirety.

FIELD

The present application relates to implant devices for implantation between adjacent vertebrae and, in particular, to implant devices for immobilization and fusion of adjacent vertebrae.

BACKGROUND

A variety of spinal conditions result in a person experiencing pain or limited physical activity and ability. More specifically, damage to vertebrae composing the spine and spinal discs between the vertebrae may occur as a result of trauma, deformity, disease, or other degenerative conditions. Some of these conditions can be life-threatening, while others cause impingement on the spinal cord resulting in pain and a lack of mobility. Removing the impingement, thus reducing swelling or pressure from the damaged or diseased tissue against the spinal cord, can relieve the pain and often promotes healing and return of normal nervous system functioning. However, the absence of proper medical care may lead to further damage and degeneration of spinal health and to permanent spinal cord damage.

The spine principally includes a series of vertebrae and spinal discs located in a space between adjacent vertebrae. The vertebrae are formed of hard bone while the discs comprise a comparatively soft annulus and nucleus. The discs support the vertebrae in proper position and enable the torso to be rotated and to bend laterally and anteriorly-posteriorly. The discs also act as shock absorbers or cushions when the spine is experiencing shock, such as when a person jogs.

Damage to the spine often results in a reduced physiological capability. For instance, damage to the disc may allow the annulus to bulge, commonly referred to as a herniated disc. In more severe cases, the damage may allow the nucleus to leak from the annulus. These same results may be brought about by a damaged or fractured vertebra. In any event, such damage often causes the vertebrae to shift closer or compress, and often causes a portion of the disc to press against the spinal cord.

One manner of treating these conditions is through immobilization of the vertebrae in a portion of the spine, such as two or more adjacent vertebrae. The conditions often lead to degeneration and a loss of disc support, and immobilization is often beneficial in reducing or eliminating pain. Immobilization and/or fusion have been performed via a number of techniques and devices, and the type of injury often suggests a preferred treatment regime.

One of these treatments is known as spinal fusion surgery. For this, two or more adjacent or consecutive vertebrae are initially immobilized relative to each other and, over time, become fused in a desired spatial relationship. The vertebrae are relatively immobilized at the proper intervertebral distance which replicates the support characteristics of the spine. This prescription sacrifices the rotation or flexion between the affected vertebrae, such that some loss of movement and flexibility is experienced. However, the compression on the spinal cord due to the injury or damage is reduced or eliminated, and the fused vertebrae protect the spine and spinal cord from injury. Overall, the non-fused portions of the spine are largely able to compensate for most normal movement expected by a patient.

Currently, a number of vertebral body replacement devices (VBRs) for immobilizing and fusing adjacent vertebrae are known. During an implantation procedure, the intervertebral space is initially excavated to provide a volume for locating a VBR therein. Once excavated, the adjacent vertebrae have a tendency to shift toward each other a small amount, thereby compressing the space or volume. Additionally, many VBRs have surface features such as prongs or teeth which extend away from upper and lower surfaces of the VBR for being embedded into the adjacent vertebrae. In order to locate the device within the intervertebral space, instruments may be used to spread the vertebrae apart. During such a procedure, care must be taken not to damage the spinal cord. The VBRs may then be inserted into the intervertebral space in an orientation where the surfaces with teeth thereon face the adjacent vertebral surfaces. However, the teeth may impede insertion of the VBR by biting into the bone too much. Alternatively, the VBR may not be maintained in position if the teeth do not bite into the bone enough to impede movement or walking of the VBR when installed.

Further, oftentimes spacing between vertebrae is not uniform such that differently shaped VBRs may be inserted. In this regard, it may be possible that two vertebrae have a large gap on the patient's right side while two other vertebrae in the same patient may have a large gap on the patient's left side. In such situations, where lateral insertion of the VBR is being used, the surgeon must go in on opposite sides of the patient or otherwise rotate the patient to insert the VBRs in between the oppositely shaped sets of vertebrae. This is a result of a number of features such as the shape of the VBRs and the location of the tool coupling locations.

In some cases, the intervertebral space receives the VBR or implant device as well as an amount of graft material. The graft material may be in a number of forms, such as cancellous bone chips, which are packed into the intervertebral space and around the VBR. For VBRs with internal cavities opening on at least one side to the intervertebral space, graft material is also placed within the cavities so that bone may grow through the VBR device and join with bone formation throughout the intervertebral space.

However, as these bone chips are loose and oftentimes fragile, migration of the bone chips from the intervertebral space presents an issue. While implanting more bone graft material promotes faster bone formation throughout the intervertebral space, the loose bone chips or graft material portions tend to separate from each other, a tendency which is exacerbated by being more tightly packed. Full fusion may take upwards of two years, during which time a patient's movement may contribute to the graft material explanting from the intervertebral site. In general, previous solutions to this problem have consisted of sewing the intervertebral site closed, such as by retaining and re-closing the natural damaged annulus, or by providing the cavities within a VBR.

Accordingly, there has been a need for improved spinal fusion systems.

SUMMARY

Thus, in accordance with one form, an intervertebral implant for being implanted between adjacent vertebrae is provided. The implant includes a generally elongate implant body having a length extending between opposite longitudinal ends thereof, a superior face and an inferior face. The superior face and inferior face include cortical teeth adjacent to the implant body longitudinal ends and have bone-engaging ends for engaging outer cortical bone material of the vertebrae. Additionally, the superior and inferior faces include longitudinally central teeth intermediate the cortical teeth and have bone engaging ends for engaging central bone material of the vertebrae that are softer than the cortical bone material thereof with the central teeth bone engaging ends having a sharper configuration than that of the cortical teeth bone engaging ends for biting into the softer central bone material of the vertebrae.

In accordance with one form, an intervertebral implant is provided having an implant body. A superior face of the implant body includes a first end, a second end and a central portion positioned between the first and second ends. An inferior face of the implant body includes a first end, a second end and a central portion positioned between the first and second ends. Different cortical and central teeth on at least one of the superior and inferior faces are configured in an osteo-specific arrangement with at least one of the first and second ends including a first density of the cortical teeth per unit area and the central portion including a second density of the central teeth per unit area, the first density being greater than the second density.

According to one form, an intervertebral implant for insertion between adjacent vertebrae is provided. The intervertebral implant includes a generally elongate implant body having a length extending between opposite longitudinal ends thereof. Further, a thick body portion is located at one of the implant body ends and has a first insertion tool attachment portion. A thin body portion is at the other implant body end so that the implant body generally tapers down from the one end to the other end thereof. A longitudinal gap in located the thin body portion open to the other end of the implant body for receiving an insertion tool therein. A transverse wall portion of the implant body is intermediate the longitudinal ends thereof with the longitudinal gap terminating at the transverse wall portion. Additionally, the transverse wall portion has a thickness greater than the thin body portion. A second insertion tool attachment portion of the transverse wall portion is provided to which an insertion tool received in the longitudinal gap can be attached for inserting the implant body either utilizing the first insertion tool attachment with the thin body portion leading during implant insertion or utilizing the second insertion tool attachment portion with the thick body portion leading during implant insertion.

An intervertebral implant is provided for insertion between adjacent vertebrae. The implant includes an implant body having a length extending between opposite longitudinal ends thereof. Further, the implant includes a superior face of the implant body and an inferior face of the implant body. A throughbore extends between the superior and inferior faces through the body and is configured to receive fusion material therein. The implant also includes an interior wall of the implant body extending along the throughbore and is configured to retain the fusion material therein. A plurality of first stabilizing protrusions extend from the interior wall in a first orientation to impede the fusion material from exiting the aperture to the superior face during a surgical implant procedure. Further, a plurality of second stabilizing protrusions extend from the interior wall in a second orientation to impede fusion material from exiting the aperture to the inferior face during the surgical implant procedure. In this regard, the first and second orientations are different.

DETAILED DESCRIPTION

Figure 1:
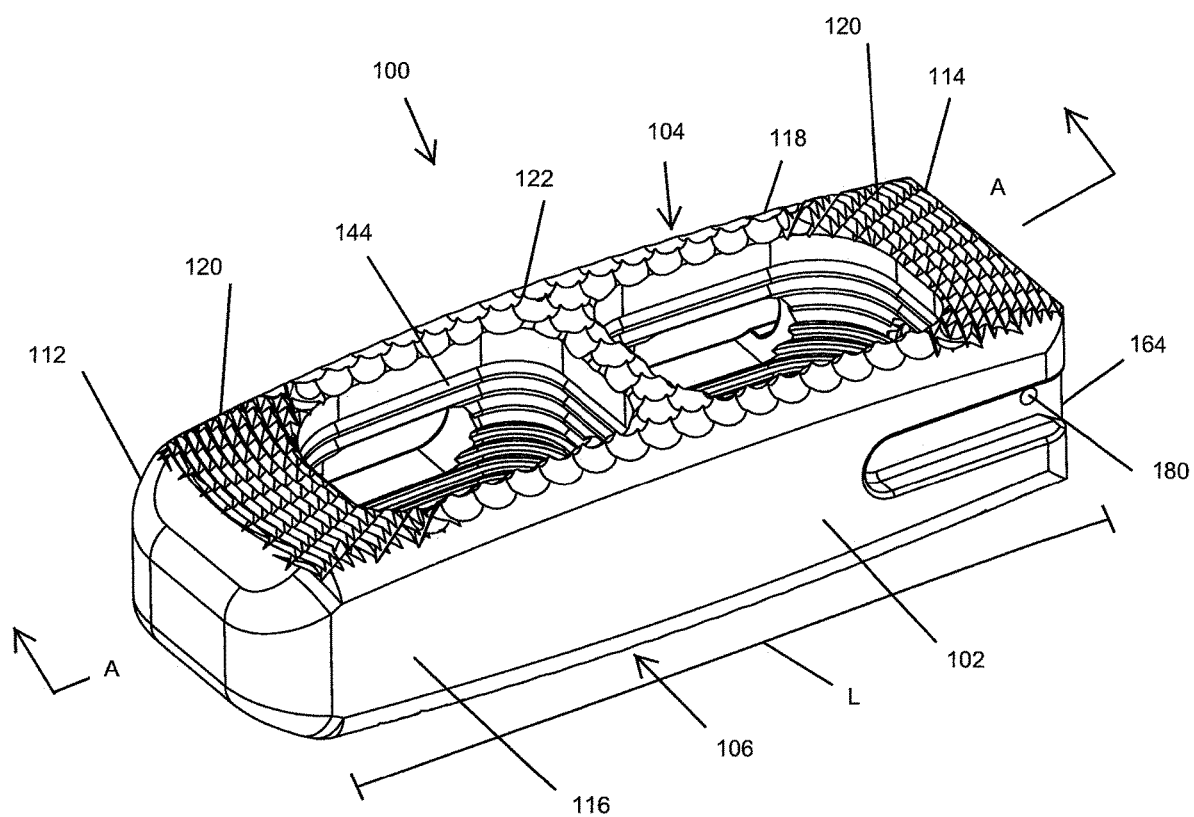
FIG. 1 is a perspective view of one form of an intervertebral implant.

Referring initially to FIG. 1, one form of an intervertebral implant is shown for implantation within an intervertebral space between adjacent vertebrae, such as used during fusion surgery. More specifically, implant 100 is illustrated as having a body 102, a superior face 104 and an inferior face 106. The superior 104 and inferior 106 faces may have a gentle convex curvature to generally match the concave curvature of the vertebrae when installed. These faces may be parallel, or inclined at an angle with respect to each other as will be understood from the description and additional embodiments described below and illustrated in the figures.

For example, the implant may be configured in a 'D' profile, wedge profile, bullet-shaped profile and the like. In one form, the implant may be configured with profiles comprising a narrower lateral dimension along its axis of insertion into the intervertebral space therein minimizing disruption to tissue. Conversely, since the device must act as a spacer, it must provide adequate support to the superior and inferior endplates of the corresponding vertebrae such that stresses do not cause the device to subside into the endplate bone. Therefore, the device should avoid unduly narrow or otherwise unstable profiles with inadequate endplate supporting surfaces. It should be noted that other shapes, sizes and the like are contemplated.

Implant angulation may also be orientated from a shorter first end face or nose face to a taller second end face or trailing face as in the coronal taper which will be discussed in more detail regarding other embodiments described herein. The slope of the implant may be configured to correct spinal deformities wherein the bone is deformed or diseased such that one side of the intervertebral space is open wider than the other or in which one side of a vertebrae needs to be jacked up in order to realign a vertebral segment. Moreover, the implant may be angled or beveled along any respective face or wall to accommodate differently shaped vertebrae.

Figure 4:
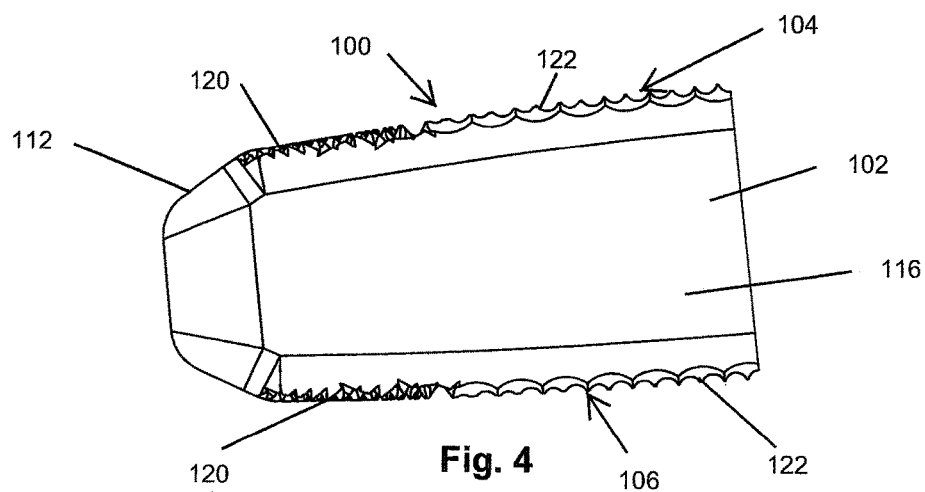
FIG. 4 is an enlarged side view of a portion of the intervertebral implant of FIG. 1.
Figure 5:
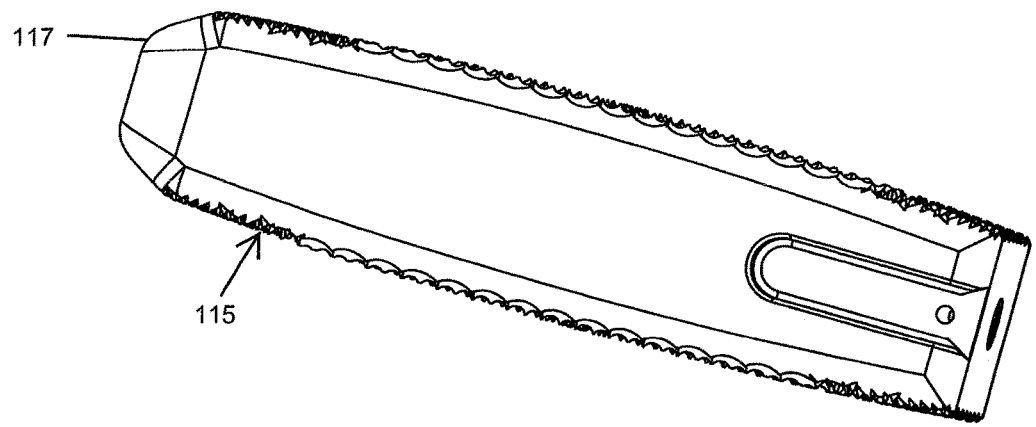
FIG. 5 is a side view of a further intervertebral implant.
Figure 6:
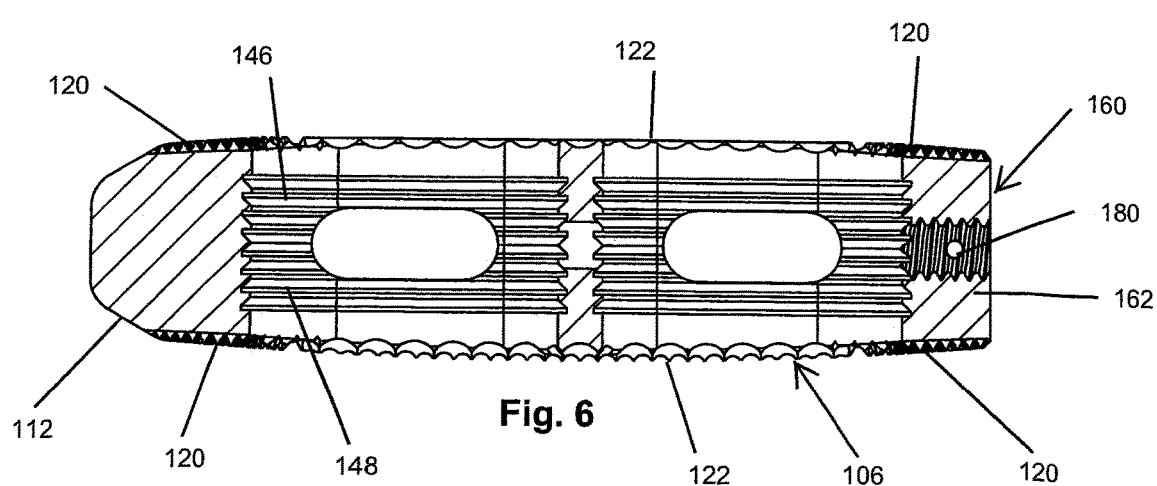
FIG. 6 is a cross-sectional view taken along line A-A of FIG. 1.

In one form, the body 102 generally includes a length (L) extending between opposite longitudinal ends 112, 114. In one form, the longitudinal end 112 may be considered generally a nose end while end 114 may be considered a tail end. As best seen in FIGS. 1 and 4, the end 112 may be generally arcuate shaped, beveled or otherwise tapered to assist in distracting adjacent vertebrae during insertion. In this regard, the end 112 slopes away from or otherwise curves away from the respective superior and inferior faces 104, 106. A further implant 115 is shown in FIG. 5 having a more rounded end 117 compared to end 112. Other shapes and sizes of the ends are also contemplated, such as will be described below in further detail with respect to additional embodiments found in the figures. The body 102 may also include side walls 116,118, depending on the shape of the body 102.

The implant 100 may include a plurality of different teeth, such as cortical teeth 120 and central teeth 122. The cortical teeth 120 and central teeth 122 may be configured and positioned to interact with different bone materials and densities as will be discussed in more detail below.

Figure 2:
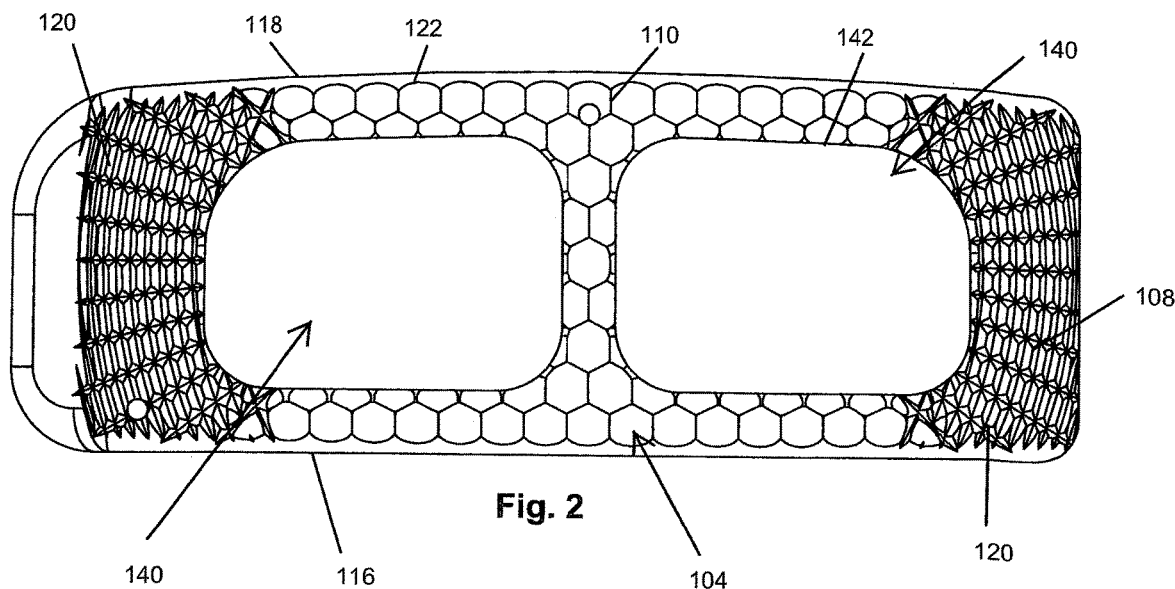
FIG. 2 is a top view of the intervertebral implant of FIG. 1.
Figure 3:
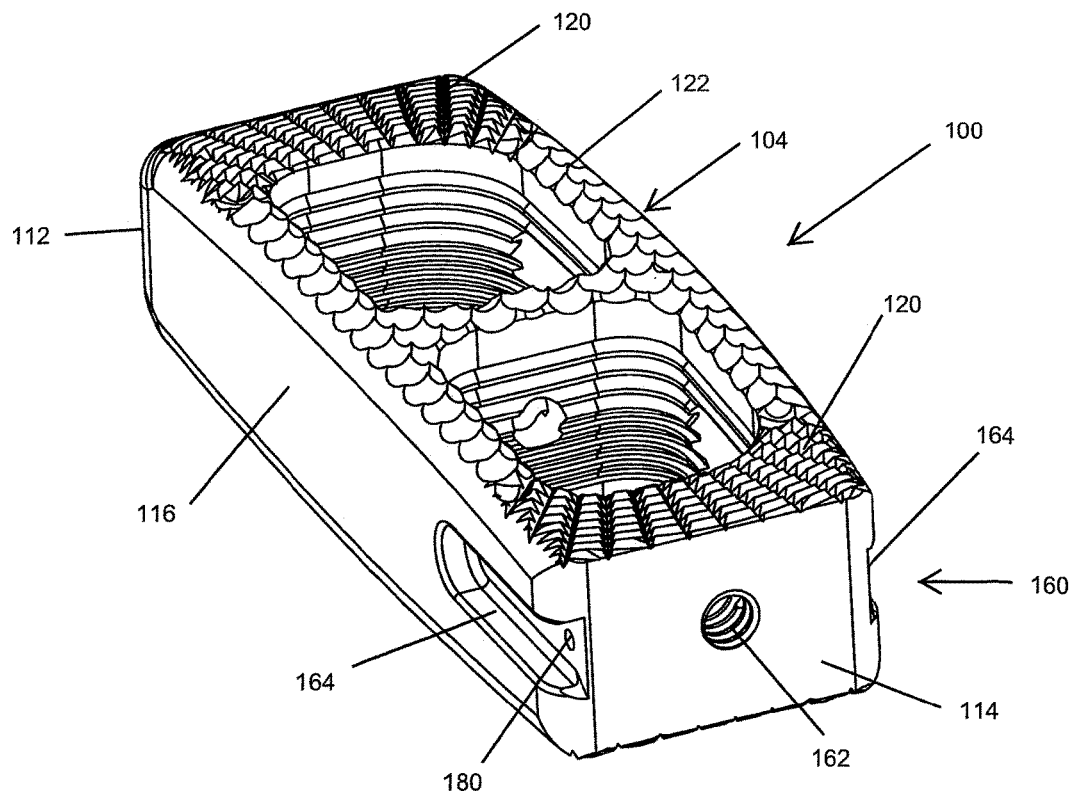
FIG. 3 is a rear perspective view of the intervertebral implant of FIG. 1.
Figure 8:
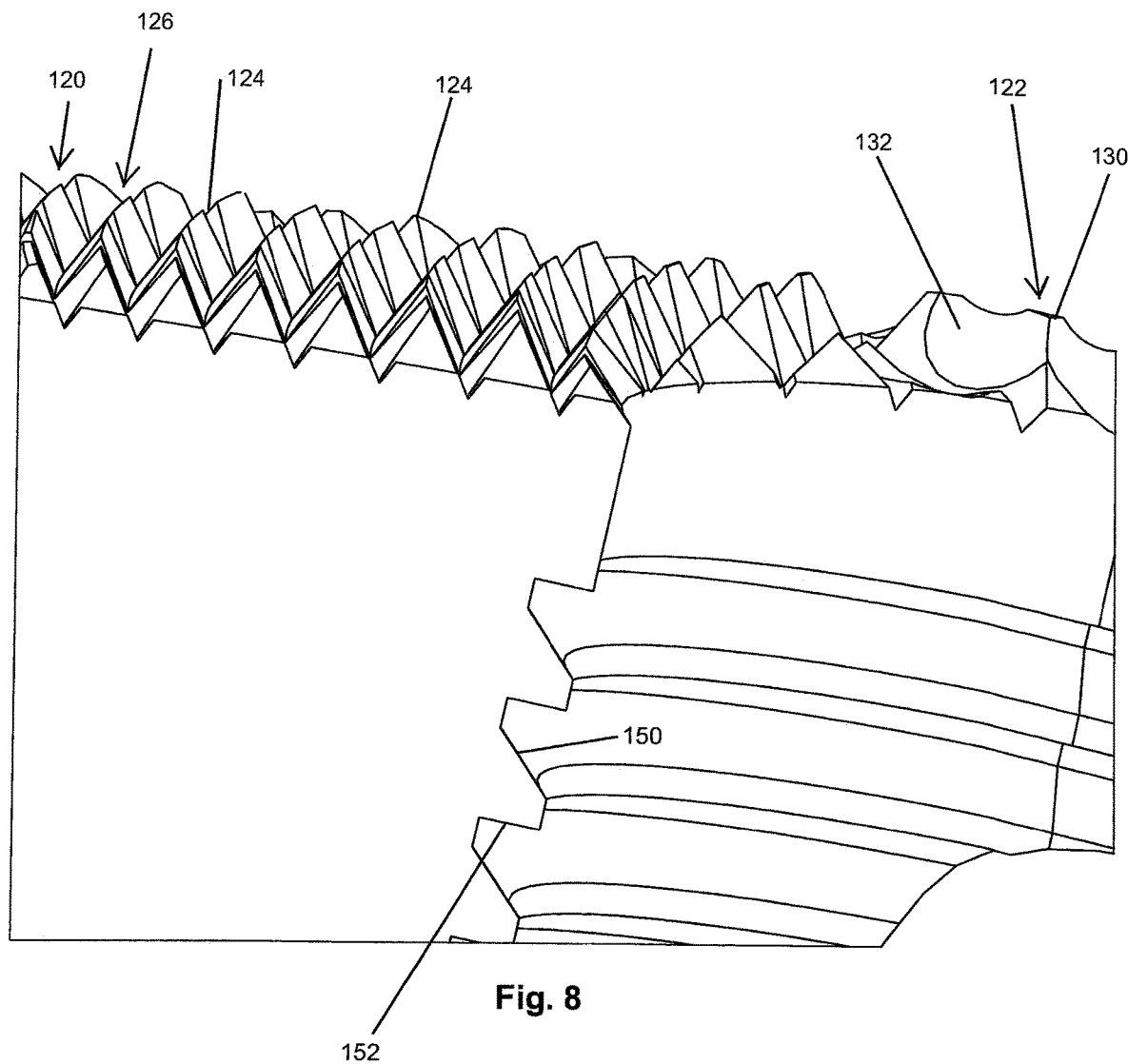
FIG. 8 is an enlarged perspective view of a portion of the cross-section taken along line A-A of FIG. 1.
Figure 9:
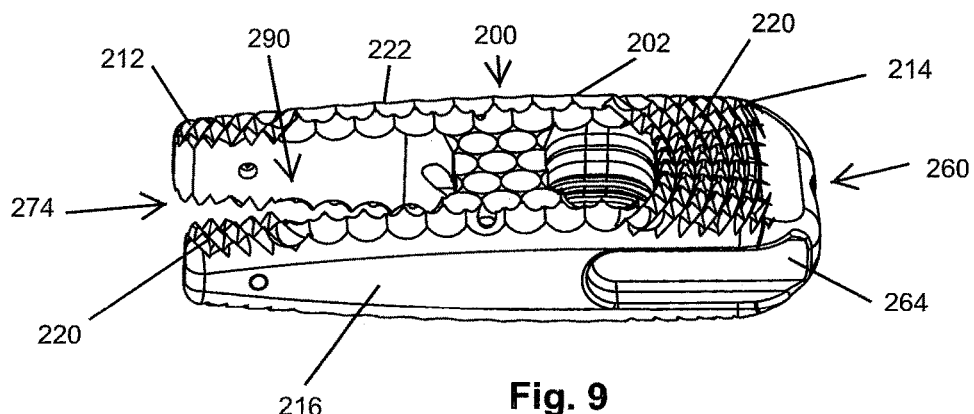
FIG. 9 is a perspective view of one form of an intervertebral implant.
Figure 10:
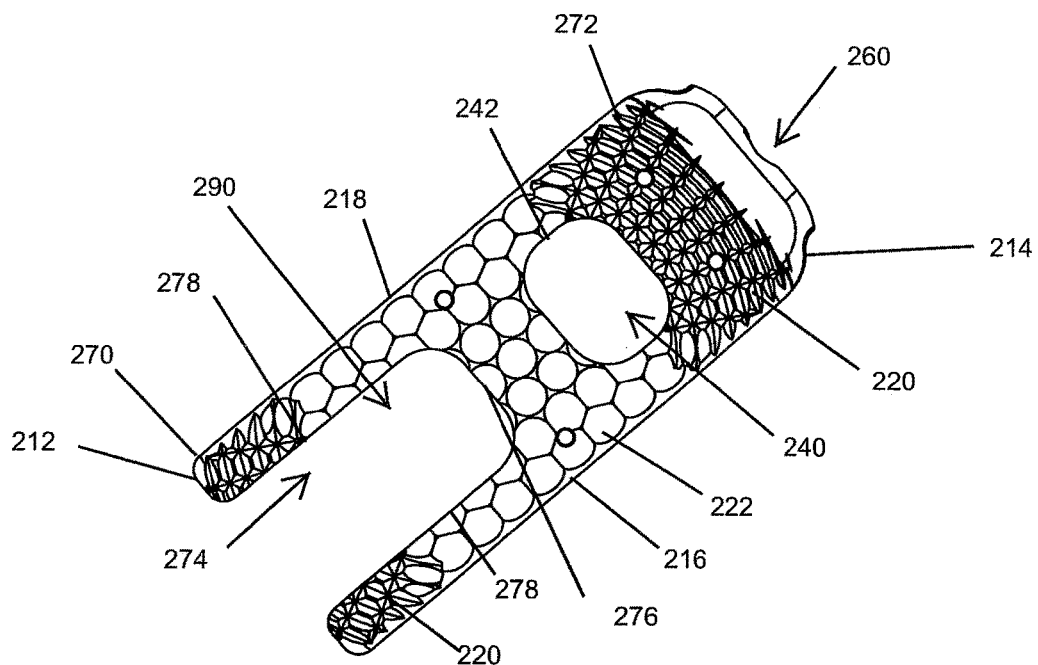
FIG. 10 is a top view of the intervertebral implant of FIG. 9.

As seen in FIGS. 1-3, in one form, cortical teeth 120 may be positioned on one and/or both of the superior and inferior faces 104,106. Further, the cortical teeth 120 may be positioned adjacent the longitudinal ends 112,114 so as to engage outer cortical bone when installed. In this regard, the cortical teeth 120 may include bone engaging ends 124, such as peaks of the teeth 120, which are configured for contacting the relatively hard cortical bone material when installed. The bone engaging ends 124 need not be sharp as they are configured for contacting the cortical bone. In one form, the bone engaging ends 124 are flattened, as seen in FIG. 8, or are otherwise rounded or the like to provide contact surfaces for contacting cortical bone.

Figure 7:
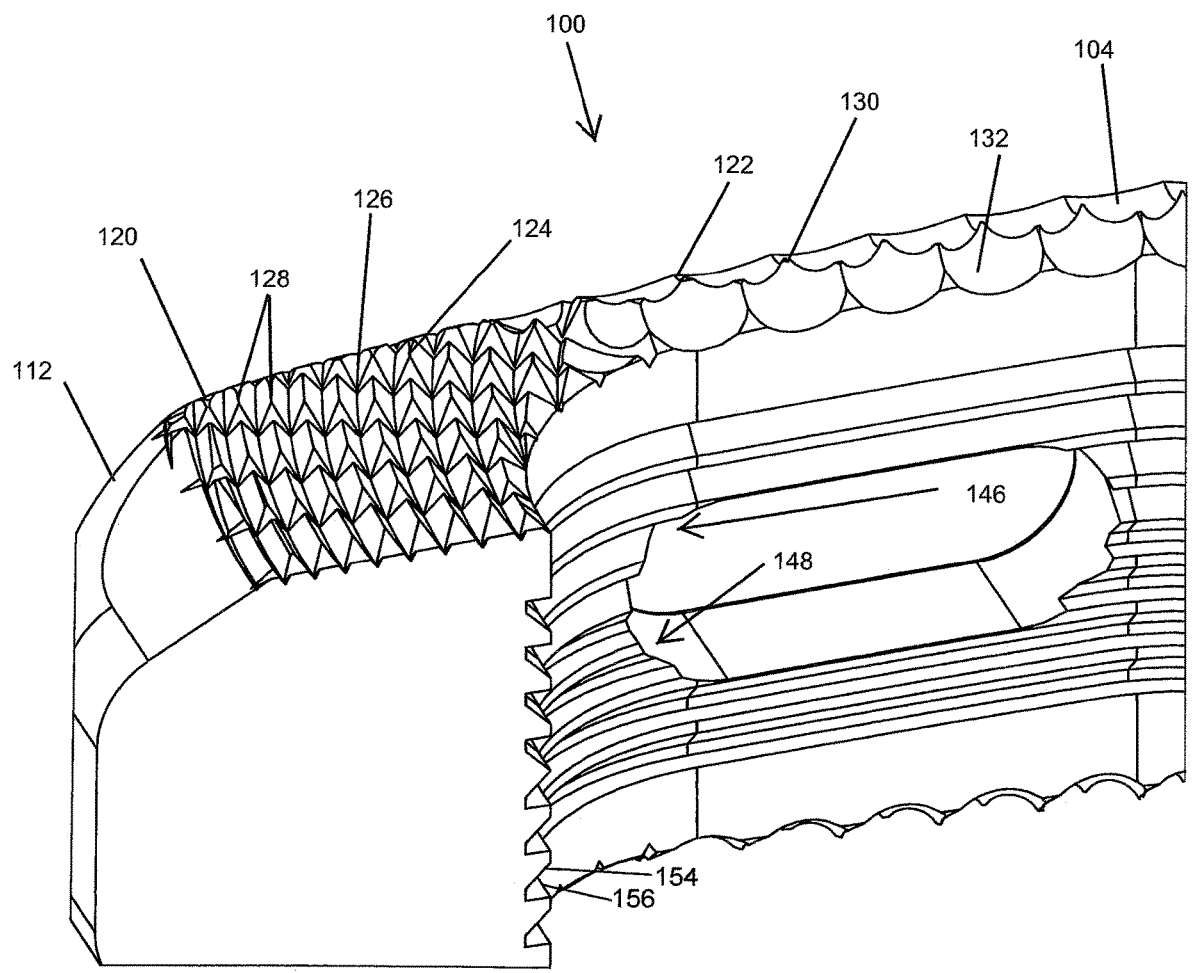
FIG. 7 is an enlarged perspective view of a portion of the cross-section taken along line A-A of FIG. 1.

The cortical teeth 120 also include valleys 126 between the teeth. The valleys 126 may be in the form of grooves, channels and the like to help separate and define the individual cortical teeth 120. The valleys 126 may also be used to help define a number of different rows 128 of cortical teeth 120. As shown in FIG. 7, the cortical teeth 120 may be arranged in a number of rows 128 wherein the rows are generally arranged in an arcuate manner. In this regard, the arcuate arrangement of the cortical teeth may be configured such that the cortical teeth 120 generally conform to the expected location of the cortical bone when inserted into a patient.

The central teeth 122, on the other hand, include bone engaging ends 130 which are relatively sharper when compared to the cortical teeth 120. As seen in FIGS. 7 and 8, the bone engaging ends 130 of the cortical teeth come to a much sharper point or peak when compared to the bone engaging ends 124 of the cortical teeth 120. In this regard, the central teeth 122 may be better suited for biting into the central bone region which is relatively softer compared to the cortical region. Just as with the cortical teeth 120, the central teeth also include valleys 132 to define the individual central teeth 122. The valleys 132 may also take a variety of different shapes and sizes. For example, as shown in FIG. 7, the valleys 132 are generally bowl shaped to define the bone engaging ends 130. In this regard, each valley 132 may be used to define a plurality of different bone engaging ends 130 or peaks. In one form, each valley may be bordered by at least six different peaks or bone engaging ends 130. In this form, the valleys 132 are bowl-like, but are also generally hexagonal. Other forms, shapes and sizes of the bone engaging ends 130 and valleys 132 are also contemplated.

Further, in one form, the central teeth 122 are more spaced apart from one another when compared to the cortical teeth 120. More specifically, the bone engaging ends 130 are more spaced from one another than the bone engaging ends 124. In this form, the bone engaging ends 130 of the central teeth 122 will be able to provide a greater force per unit area to bite into the softer central bone when compared to the bone engaging ends 124 of the cortical teeth biting into the cortical bone area. In other words, the density (number per unit area) of the cortical teeth 120 and/or the bone engaging ends 124 is greater than the density (number per unit area) of the central teeth 122 and/or the bone engaging ends 130.

Moreover, in one form, the cortical teeth 120 provide a greater ratio of contact surface area, such as the surface area of the bone engaging ends 124, per unit area covered by the cortical teeth 120 when compared to the contact surface area, such as the surface area of the bone engaging ends 130, per unit area covered by the central teeth 122. Further, the average distance between adjacent engaging ends 124 of the cortical teeth is smaller than the average distance between adjacent engaging ends 130 of the central teeth.

The cortical teeth 120 and central teeth 122 may also have varying heights and otherwise may extend different distances from the respective faces 104,106. In one form, the teeth 120,122 extend approximately the same distance from each of the faces 104,106. In another form, the central teeth 122 extend further from the respective faces 104,106 when compared to the cortical teeth 120. In yet another form, the cortical teeth 120 extend further from the respective faces 104,106 when compared to the central teeth 122. It should also be understood that the faces 104,106 may be curved, tapered and the like such that the teeth 120,122 may be relatively flat or may otherwise follow the contour of the faces 104,106.

As described above, the cortical teeth 120 and central teeth may be configured in a number of different manners to contact specific portions of bone when inserted into a patient. For example, the cortical teeth 120 and central teeth may be configured in an osteo-specific tooth pattern. This pattern coincides with the bone type of the intervertebral endplate. The cortical teeth 120 are positioned adjacent denser bone at the cortical rim of the endplate, whereas the larger and sharper central teeth 122 reside more centrally where the softer endplate bone is located. In one form, unlike other devices which may have teeth configured to prevent implant backout, this osteo-specific tooth configuration may be utilized to restrict implant movement in all directions.

The implant 100 may also include one or more throughbores 140 on an interior wall 142 of the implant body 102. The throughbores 140 may be configured to receive bone graft, bone substitute, or other similar material. To assist in maintaining the bone graft, bone substitute, or similar material in the throughbore 140, a plurality of stabilizing protrusions 144 may be included therein. The protrusions 144 may take a variety of forms such as recesses, grooves, bosses, or fins formed within the throughbore 140 so as to interfere with packed graft sliding out. As found in the figures, the protrusions 144 are in the form of ridges extended generally around the circumference of the throughbore 140. The protrusions 144 are configured to be deep enough to stabilize the graft yet shallow enough so as to not substantially reduce the size of the throughbore 140 therein reducing the strength of the fusion.

In one form, such as shown in FIGS. 7 and 8, the throughbore 140 includes a first plurality of protrusions 146 configured in a first orientation and a second plurality of protrusions 148 configured in a second orientation. According to one form, the first and second protrusions 146,148 are essentially the same type and form of protrusions, simply oriented in different configurations. For example, the first protrusions 146 include an angled surface 150 relative to the superior face 104 and a generally parallel face 152 relative to the superior face 104. In this regard, the angled surface 150 will permit bone graft material to be inserted from the superior face 104 side of the implant 100, but the generally parallel face 152 will impede bone graft material from exiting the throughbore 140 to the superior face 104.

The second plurality of protrusions 148 may include similarly structured protrusions, just configured in a generally mirror image manner compared to the first plurality of protrusions 146. For example, the second plurality of protrusions 148 may include an angled surface 154 relative to the inferior face 106 and a generally parallel face 156 relative to the inferior face 106. The angled surface 154 will permit bone graft material to be inserted from the inferior face 106 side of the implant 100, but the generally parallel face 156 will impede bone graft material from exiting the throughbore 140 to the inferior face 106. In one form, the first and second pluralities of protrusions 146,148, are positioned and extend from a midpoint about the longitudinal length of the implant 100. In other words, the generally parallel faces 152,156 will be positioned such that they face the midpoint extending along the longitudinal axis of the implant.

In one form, such as shown in FIGS. 1 and 2, the implant 100 may include a plurality of throughbores 140, such as two throughbores 140. However, the implant 100 may include a single throughbore 140 or no throughbores 140. Further, in the case of multiple throughbores 140, the sizes and shapes of the throughbores 140 need not be the same. For example, one throughbore 140 may be wider and longer than another throughbore 140. Similarly, different throughbores 140 may have different heights, extending from the superior face 104 to the inferior face 106.

Further, the body 102 may include an insertion tool attachment portion 160. The insertion tool attachment portion 160 may be positioned at either and/or both of the ends 112,114. As shown in FIGS. 1 and 3, the insertion tool attachment portion 120 is positioned at the end 114.

The insertion tool attachment portion 160 may comprise recesses, grooves, bosses, holes, threads, posts or other features that can be used to secure the implant 100 to an elongated instrument. The implant in FIG. 3 utilizes a threaded hole 162 that may extend through one or more walls at the end 114 along with one or more arm pockets 164. Together these features are configured to house the distal end of an implant inserter comprising an elongated shaft with a U-shaped end. Central to the U is a threaded rod for engagement into the threaded hole 162 to pull the implant tight to the instrument. The arms of the U are spaced and configured to be received in the one or more arm pockets 164 to control rotational stability and to limit bending stress on the threaded rod from the instrument that threads into the threaded hole 162 of the implant 100.

A further form of an implant is illustrated in FIGS. 9-12. It should be noted that similar features found in this embodiment will be given similar numbers to those features previously described. More specifically, an implant 200 is provided having a body 202, a superior face 204 and in inferior face 206. As most readily seen in FIG. 11, the superior 204 and inferior 206 faces may include a gentle curvature. The body 202 also includes longitudinal ends 212,214.

Figure 11:
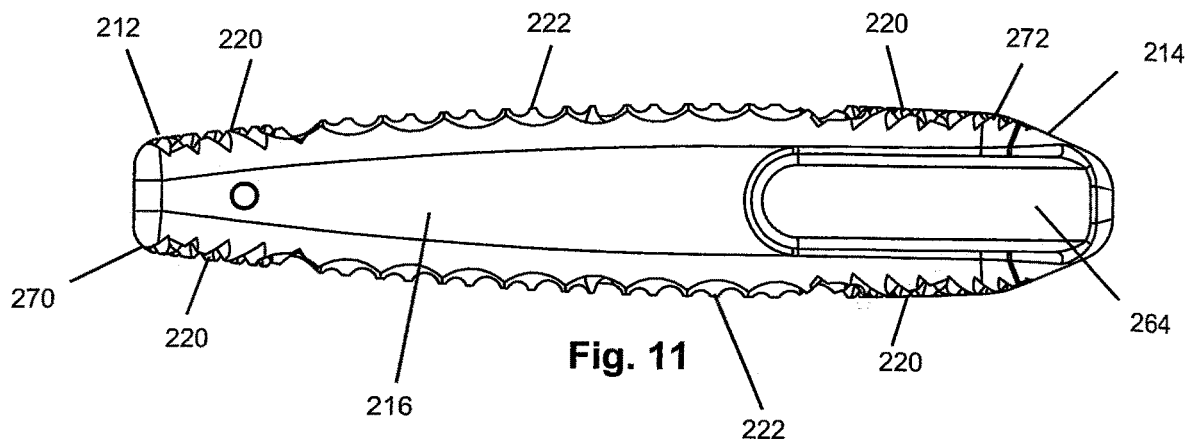
FIG. 11 is a side view of the intervertebral implant of FIG. 9.
Figure 12:
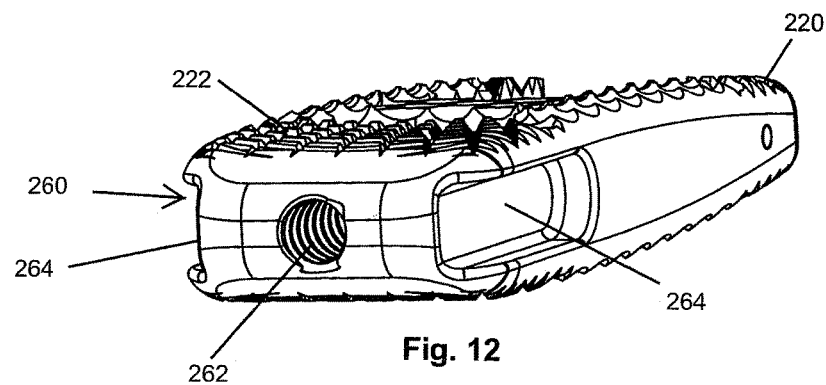
FIG. 12 is a rear perspective view of intervertebral implant of FIG. 9.

Further, the faces may be configured and positioned such that the body is somewhat tapered. In this regard, a thin body portion 270 may be at end 212 while a relatively thick body portion 272 may be at the other end 214. The body 202 may also include side walls 216,218. As shown in FIG. 11, the body 202 generally tapers down from end 214 towards end 212. Further, it should be noted that end 212 is somewhat beveled or otherwise arcuate, but need not be as beveled or arcuate as the embodiment shown in FIG. 1 as end 212 is a thin portion 270 that, as a result of its shape and taper, will assist in distracting adjacent vertebrae. Therefore, end 212 may be inserted as a leading edge into a patient.

As seen in FIG. 11, the end 214 is beveled, tapered, arcuate or otherwise configured to assist in distracting adjacent vertebrae. In this regard, the implant 200 may be considered a bi-directional implant as it may be inserted with either of end 212 or end 214 as the leading edge during insertion as either end 212,214 will assist in distracting adjacent vertebrae. Just as with implant 100, implant 200 may take a variety of shapes, sizes, configurations and the like.

Further, implant 200 may also include cortical teeth 220 and central teeth 222 similar to the manner and features described above with respect to the embodiment of FIG. 1. The cortical teeth 220 and central teeth 222 may be configured and positioned in an osteo-specific manner to provide interact with different bone materials and densities as discussed above.

The cortical teeth 220 include bone engaging ends 224 and valleys 226 between the teeth 220 which may be used to help define a number of different rows 228 of cortical teeth 220. The central teeth 222 include bone engaging ends 230 which are sharper when compared to the bone engaging ends 224 of the cortical teeth 220. The sizes, shapes, positioning, functionality and other features of the cortical teeth 220 and central teeth 222 may be similar to those described above with respect to the embodiment of FIG. 1.

The implant 200 may also include one or more throughbores 240 on an interior wall 242 of the implant body 202.

The througbores 240 may include similar features, including protrusions 244 in a similar arrangement and configuration as described above.

The implant 200 may include a longitudinal gap 274 in the thin body portion 270 open to the end 212. In this regard, the longitudinal gap 272 may terminate at a transverse wall portion 276 that is intermediate the longitudinal ends 212, 214. Therefore, the longitudinal gap 272 may be a generally U-shaped gap defined by the transverse wall portion 276 and side arm portions 278. It should be noted that the transverse wall portion 276 is positioned away from the far-most portion of end 212 so that the transverse wall portion 276 has a thickness greater than the thin body portion 270.

The implant 200 may include one or more insertion tool attachment portions. As found in FIGS. 9-21, the implant 200 includes two insertion tool attachment portions. A first tool attachment portion 260 may be provided at end 214, similar to insertion tool attachment portion 160. In this regard, the first insertion tool attachment portion 260 may include a variety of different structures to couple to an insertion tool. For example, the first insertion tool attachment portion 260 includes a threaded hole 262 and one or more arm pockets 264. The first insertion tool attachment portion 260 may be configured in a similar manner to portion 160 described above and use a similar tool to thereby provide end 212 as an insertion leading edge.

The implant 200 may also include a second insertion tool attachment portion 290. In one form, the second insertion tool attachment portion 290 may be located adjacent the transverse wall portion 276. In this regard, the second insertion tool attachment portion 290 may be configured to couple to the same tool as with the first insertion tool attachment portion 260 or a different tool. In one form, the second insertion tool attachment portion 290 includes a threaded hole 292 and the longitudinal gap 274 for receiving an insertion tool. The transverse wall portion 276 and/or the side arm portions 278 may cooperate with the insertion tool to stabilize the implant during insertion.

The implants may be configured to be cooperable with a number of instruments to allow a surgeon to implant and manipulate the implant. Exemplary forms of such tools are depicted in FIGS. 13-21. In one form, a first insertion tool 300 is configured for cooperating with a first end of the implant, such as end 212. A second insertion tool 302 may be configured to cooperating with a second end of the implant, such as end 214.

In one form, the tools 300,302 are generally symmetrical in the horizontal direction, though it may alternatively be asymmetrical so that a particular relative orientation is required for coupling the implant and the insertion tool 300,302.

The insertion tools 300,302 may be used to insert the implant within the intervertebral space, and may be used for manipulation of the implant within the intervertebral space. To enable this, a distal end 320,322 of the insertion tools 300,302 and the implant are coupled in a releasable fixed orientation. The insertion tool distal ends 320,322 and the implant are coupled so that a surgeon may apply force to the insertion tool 300,302 without the implant separating therefrom.

Figure 13:
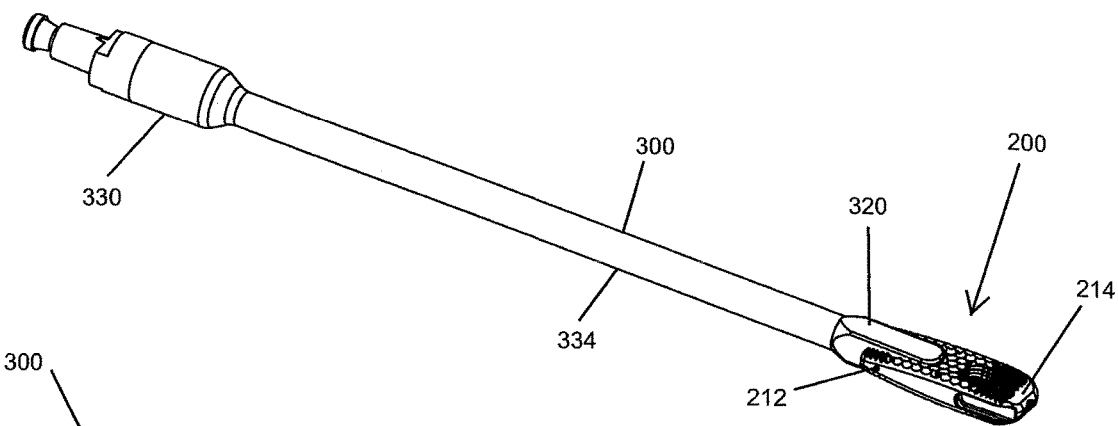
FIG. 13 is a perspective view of an intervertebral implant and insertion tool coupled to one end.
Figure 14:
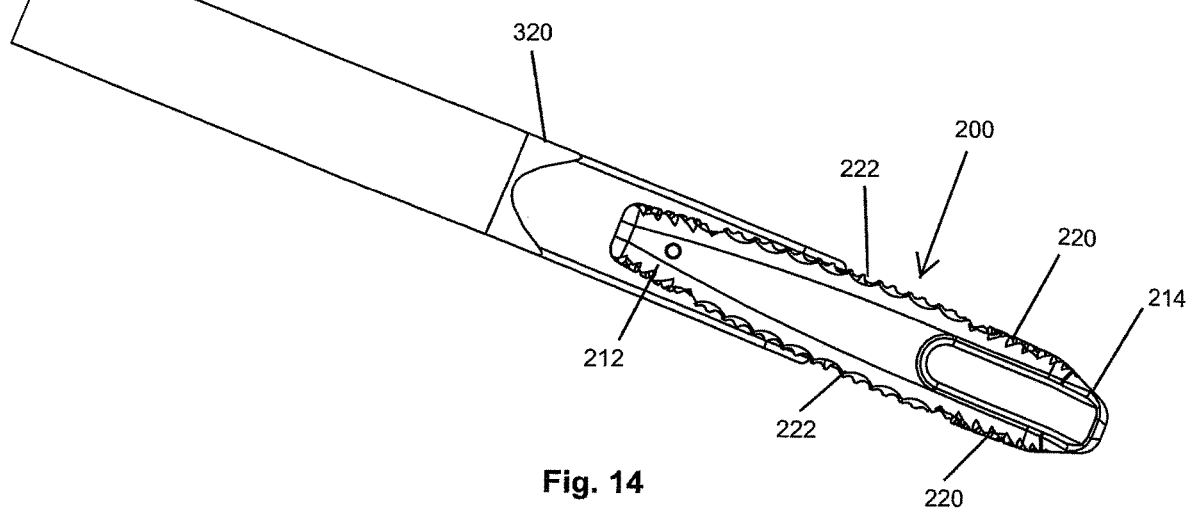
FIG. 14 is an enlarged side view of the intervertebral implant and insertion tool of FIG. 13.
Figure 15:
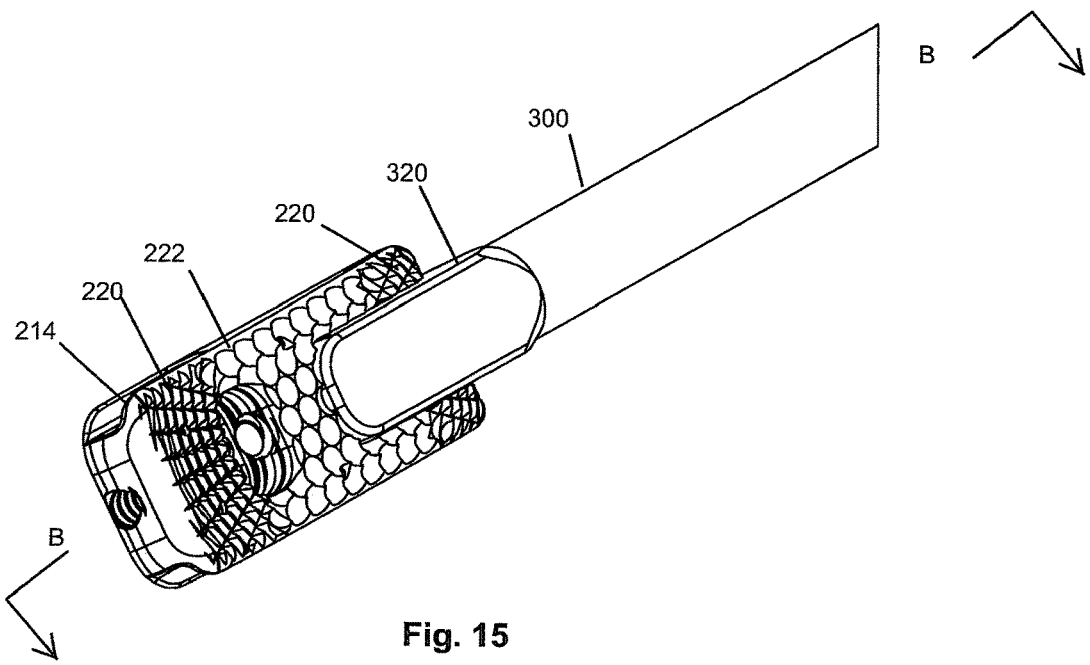
FIG. 15 is an enlarged perspective view of the intervertebral implant and insertion tool of FIG. 13.
Figure 16:
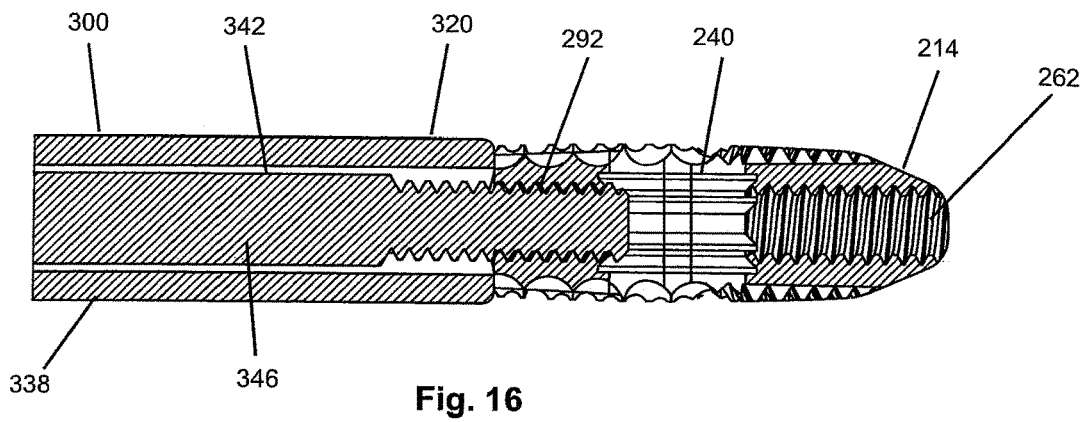
FIG. 16 is a cross-sectional view taken along line B-B of FIG. 15.
Figure 17:
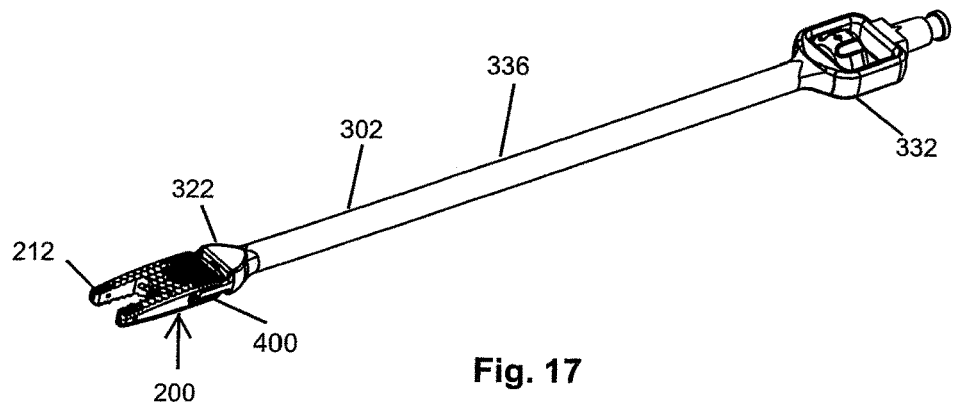
FIG. 17 is a perspective view of an intervertebral implant and insertion tool coupled to another end of the intervertebral implant.
Figure 18:
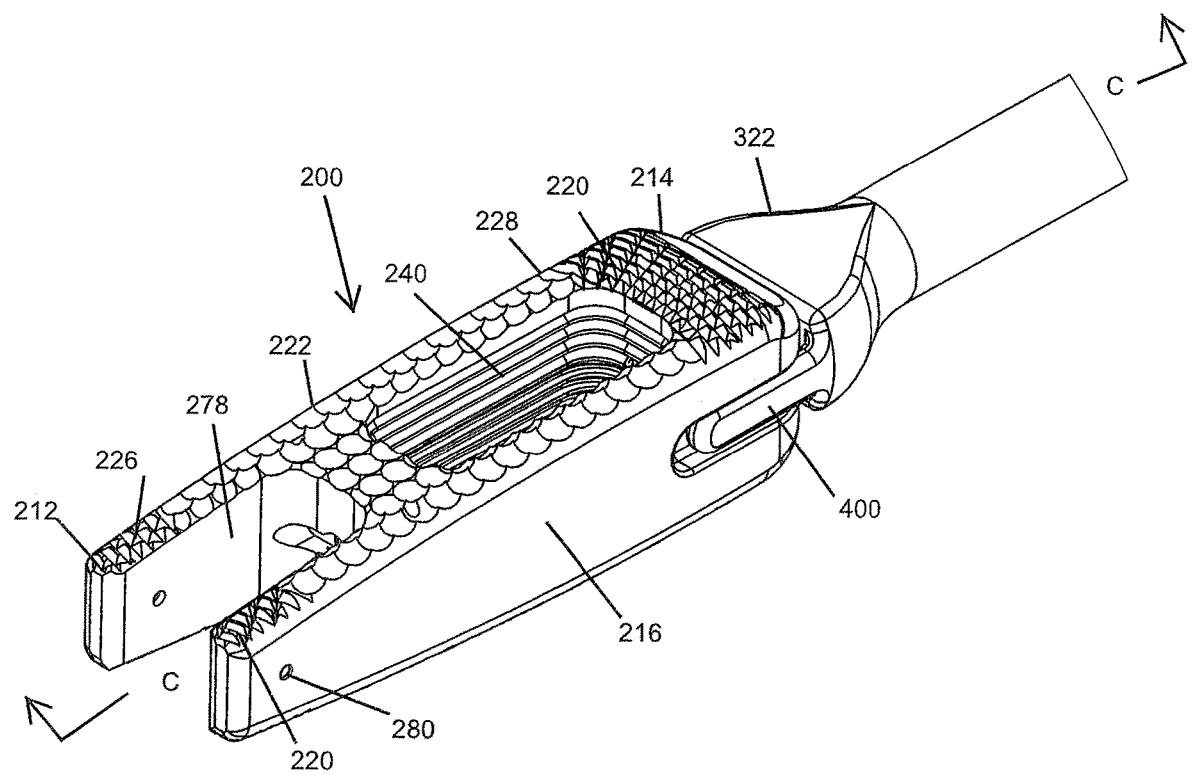
FIG. 18 is an enlarged perspective view of the intervertebral implant and insertion tool of FIG. 17.
Figure 19:
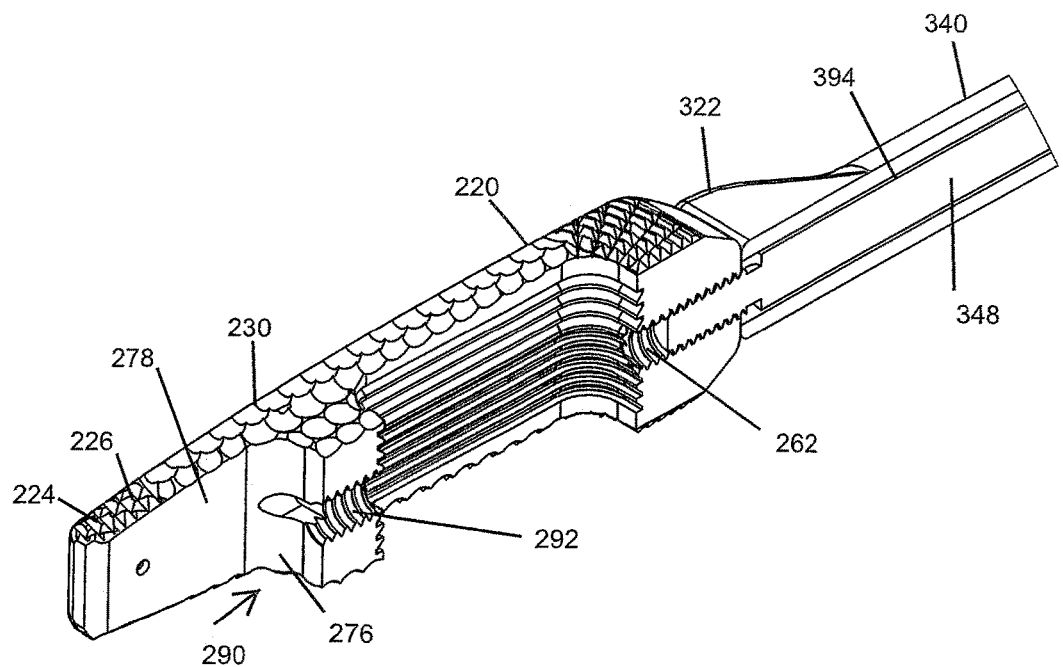
FIG. 19 is a cross-section view taken along line C-C of FIG. 18.
Figure 20:
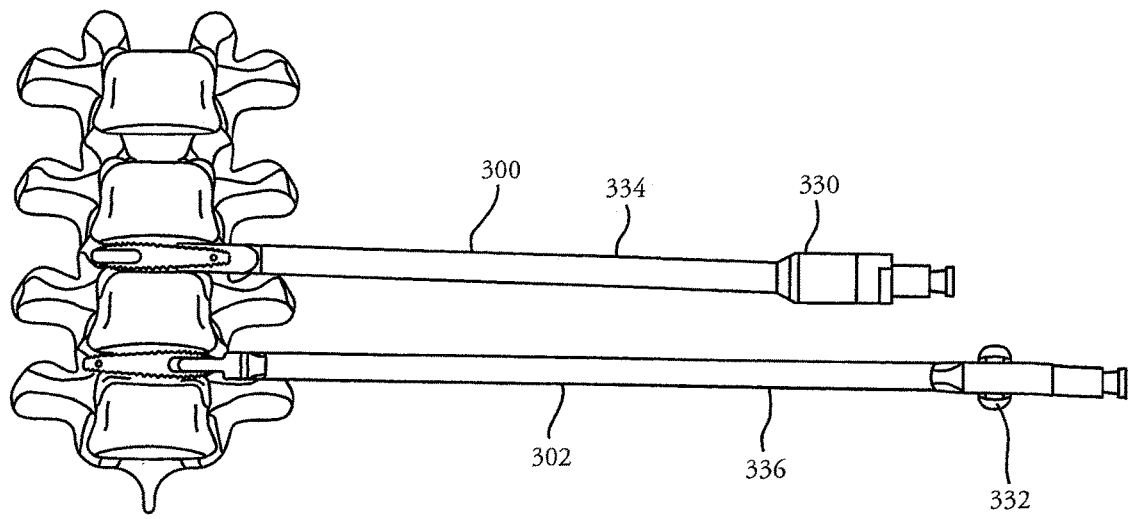
FIG. 20 is a side view of two intervertebral implants and insertion tools coupled thereto being inserted between vertebrae.
Figure 21:
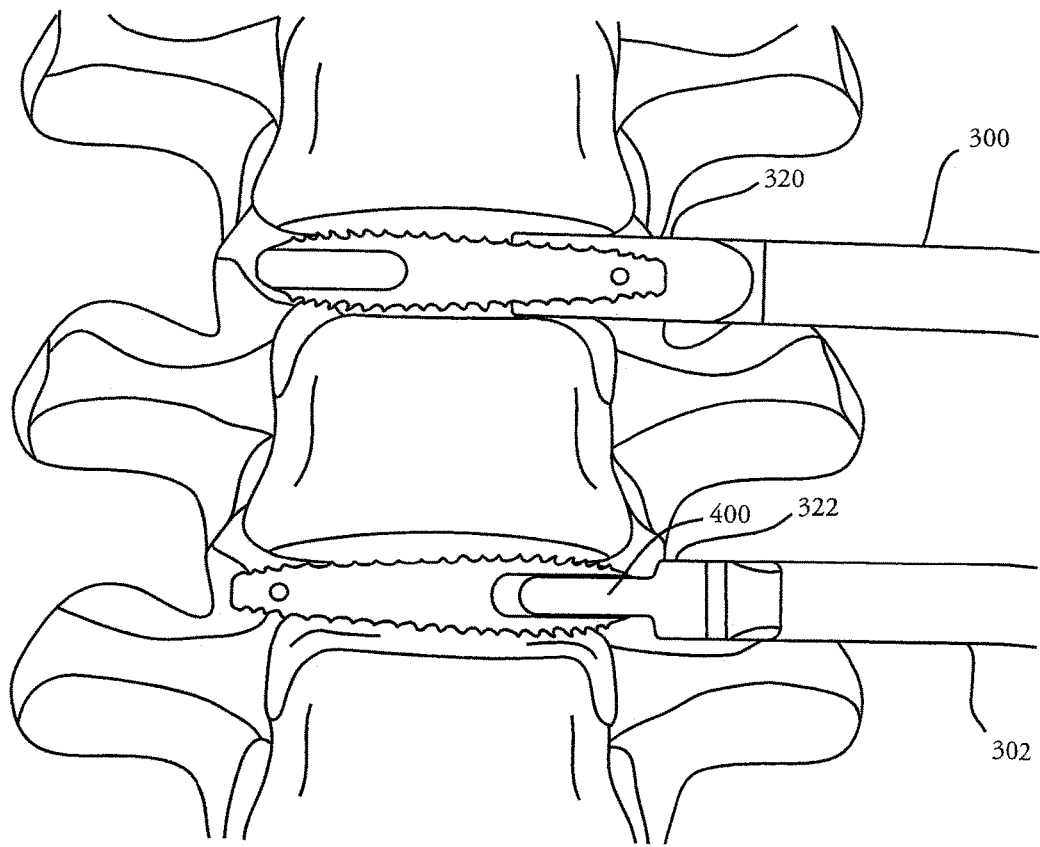
FIG. 21 is an enlarged view of the two intervertebral implants and insertion tools of FIG. 20.

Referring to FIGS. 13 and 17, the insertion tools 300,302 have a handle portion 330,332 allowing a surgeon to manipulate the coupled implant 200 and insertion tool 300,302. Extending from the handle portion 330,332 is a shaft portion 334,336 including a sheath portion 338,340 with the distal ends 320,322 engageable with the respective insertion tool attachment portions of the implant 200. The sheath portions 338,340 includes a longitudinal throughbore 342,344 in which a rod 346,348 is received. The rods 346,348 have an outer diameter sized to permit the rod 346,348 to easily rotate or reciprocate within the throughbores 342,344.

The insertion tool distal ends 320,322 are coupled with the implant 200 by engaging the rod 346,348 and the distal end 320,322 in the respective insertion tool attachment portions 260,290. For example, the rod 346 may be coupled to the threaded hole 292 while the rod 348 may be coupled to the threaded hole 262. The distal end 322 includes a pair of curved arms 400 extending outward from the distal end 322 forming a crescent-like structure which may be received by the arm pockets 264. The distal end 320 may include arms 402 which may be configured to couple to the longitudinal gap 274, the transverse wall portion 276 and/or the side arm portions 278.

Due to the anatomy of a patient, it is common and desirable to implant intervertebral fusion devices from an anterior or posterior-lateral direction, that is, from a direction offset from the lateral or anterior-posterior sides. The implant is inserted into the intervertebral space from this direction, and then the implant is manipulated into the desired orientation during insertion of the implant into the intervertebral space.

In one form, the implant is configured to lateral surgical entry. For example, in one form, the body of the implant has a height (H) which is sized upon insertion to return the intervertebral disc spacing to a height substantially the same as when spaced by a healthy intervertebral disc. The device has a length (L) substantially the lateral width of the vertebral endplate. The device also has a width (W) that is substantially less than the anterior to posterior length of the vertebral endplate and further sized for insertion down an elongated corridor to the surgical site.

The implant 200, which may be bi-directional, can be inserted from either end of the implant 200. For example, a patient having a deformity requiring a coronal implant with first end 212 leading on one level and second end or trailing end 214 leading on adjacent level could place both implants from the same incision site. A coronal implant with instrument attachment only at the second end or trailing end would require the surgeon to create a second incision on the contralateral side.

The implants described herein may also comprise additional features such as one or more marker sites 180,280. In one embodiment, the marker sites 180,280 may be in the form of a hole for the placement of a tantalum marker for viewing through X-ray or other imaging device. In this embodiment the marker pin orientation confirms anterior/posterior alignment when a 'T' shape is made with the pins. These markers 180,280 allow a surgeon to use radiographic equipment to identify the location and orientation of the implant within the intervertebral space, including identifying the height, length, and width of the implant. Utilizing the radiographic markers, a determination can be made as to whether adjustments to the position of the implant are necessary or desirable.

The implant devices described herein may be fabricated from any suitable materials having desirable strength and biocompatibility. Suitable materials may include, for example, biocompatible metals and related alloys (such as titanium and stainless steel), shape memory metals (such as Nitinol), biocompatible polymers (including, for example, materials of the polyaryletherketone family such as PEEK (polyetheretherketone), PAEK (polyaryletherketone), PEK (polyetherketone), PEKK (polyetherketoneketone), PEKEKK (polyetherketoneetherketoneketone), PEEKK (polyetheretherketoneketone), and PAEEK (polyaryletheretherketone), filled materials (such as carbon or glass fiber-reinforced materials), bone substitute materials (such as hydroxyapatite and tricalcium phosphate), composite materials, and/or any combination of the above.

In one preferred form, the implant devices are formed of a PEEK-type material. In another from, the implant device may be formed, in whole or in part, or coated with a calcium phosphate ceramic bone substitute such as hydroxyapatite, tricalcium phosphate, and/or mixtures thereof. Particularly preferred hydroxyapatite and tricalcium phosphate compositions include those disclosed in, for example, U.S. Pat. No. 6,013,591, U.S. Pat. No. RE 39,196, and U.S. Patent Application Publication No. 2005/0031704, which are hereby incorporated in their entirety herein. Coating with the calcium phosphate ceramics can be achieved by any known method, including dip coating-sintering, immersion coating, electrophoretic deposition, hot isostatic pressing, solution deposition, ion-beam sputter coating and dynamic mixing, thermal spraying techniques such as plasma spraying, flame spraying and high-velocity oxy-fuel combustion spraying. In one preferred embodiment, hydroxyapetite coating is achieved by plasma spraying.

In yet another form, the implant device may be formed of a PEEK-type material and coated with such a bone substitute material. In yet another form, the implant device may be formed, in whole or in part, coated with, injected with, incorporate, and/or retain a bone growth stimulating composition such as the bioactive hydrogel matrix described, for example, in U.S. Pat. Nos. 6,231,881, 6,730,315, 6,315,994, 6,713,079, 6,261,587, 5,824,331, 6,068,974, 6,352,707, 6,270,977, 5,614,205, 6,790,455, 5,922,339, and U.S. Patent Application Publication No. 2005/0118230, which are hereby incorporated in their entirety herein. Alternatively, the implant device of the invention may be formed of two distinct materials.

As described throughout the present application, bone graft material, bone replacement material and the like may be utilized with the implants to help fuse vertebrae. Exemplary artificial bone graft material includes calcium phosphates (such as hydroxyapatite and tri-calcium phosphate). Other suitable materials include those described in U.S. Pat. No. 6,013,591, J. Y. Ying, E. S. Ahn, and A. Nakahira, "Nanocrystalline apatites and composites, prostheses incorporating them, and method for their production," which is incorporated by reference in its entirety herein. Another exemplary material is described in U.S. Pat. No. RE 39,196 E, Jackie Y. Ying, Edward S. Ahn, and Atsushi Nakahira, "Nanocrystalline apatites and composites, prostheses incorporating them, and method for their production," which is incorporated by reference in its entirety herein.

Another exemplary product is described in U.S. Pat. No. 6,231,881 B1, Anton-Lewis Usala, and Richard Chris Klann, "Medium and matrix for long-term proliferation of cells," which is incorporated by reference in its entirety herein; and U.S. Pat. No. 6,730,315 B2, Anton-Lewis Usala, and Richard Chris Klann, "Medium and matrix for long-term proliferation of cells," which is incorporated by reference in its entirety herein; and U.S. Pat. No. 6,315,994 B2, Anton-Lewis Usala, and Richard Chris Klann, "Medium and matrix for long-term proliferation of cells," which is incorporated by reference in its entirety herein. Similarly, U.S. Pat. Nos. 6,713,079 B2, 6,261,587 B1, 5,824,331, 6,068,974, 6,352,707 B1, 6,270,977 B1, 5,614,205, 6,790,455 B2, and 5,922,339 and U.S. Patent Application 2005/0118230 A1, Ronald Stewart Hill, Richard Chris Klann, and Francis V. Lambert, "Methods and compositions for regenerating connective tissue," are incorporated by reference in their entirety herein. Further exemplary artificial bone graft materials are sold by Pioneer Surgical Technologies, Inc., under the trade names E-Matrix, TrioMatrix, Nanoss and FortrOss.

It will be understood that various changes in the details, materials, and arrangements of parts and components which have been herein described and illustrated in order to explain the nature of the methods and compositions may be made by those skilled in the art within the principle and scope as expressed in the appended claims.

What is claimed is:

1. An intervertebral implant for being implanted between adjacent vertebrae, the intervertebral implant comprising:
   a generally elongate implant body extending along a longitudinal axis between longitudinal ends, and having an intermediate portion located between the longitudinal ends;
   a pair of spaced side walls extending longitudinally along the longitudinal axis;
   a lateral wall of the intermediate portion extending transverse to the longitudinal axis;
   a superior face of the implant body;
   an inferior face of the implant body;
   the superior face and the inferior face being spaced such that the elongate implant body has a varying height as the elongate implant body extends along the longitudinal axis;
   one of the longitudinal ends being a tapered, nose end having a height less than that of the intermediate portion;
   the other longitudinal end being a tail end having a height less than that of the intermediate portion and having a tool attachment portion formed therein;
   a first throughopening of the intermediate portion between the tapered, nose end and the lateral wall and having a first interior surface including portions of the lateral wall and both sidewalls facing the first throughopening, the first throughopening opening to the superior and inferior faces and being configured to receive fusion material therein;
   a second throughopening of the intermediate portion between the tail end and the lateral wall and having a second interior surface extending thereabout including along portions of the lateral wall and both side walls facing the second throughopening, the second throughopening opening to the superior and inferior faces and being configured to receive fusion material therein;
   a plurality of protrusions extending from the first and second interior surfaces; and
   a plurality of teeth on the superior and inferior faces in the intermediate portion,
   the lateral wall at least partially separating the first and second throughopenings.

2. The intervertebral implant of claim 1 wherein the plurality of teeth are positioned in rows on the superior and inferior faces surrounding at least a portion of the first and second throughopenings.

3. The intervertebral implant of claim 2 wherein the rows of teeth are defined by valleys between the rows.

4. The intervertebral implant of claim 1 further comprising an arm pocket positioned on at least one of the longitudinal ends, the arm pocket configured to receive a portion of an insertion tool.

5. The intervertebral implant of claim 1 wherein the plurality of teeth comprise cortical teeth and central teeth.

6. The intervertebral implant of claim 1 wherein the first and second throughopenings do not communicate with each other at the superior and inferior faces of the implant body.

7. The intervertebral implant of claim 1 wherein the lateral wall extends to the superior face and the inferior face to separate the first and second throughopenings from each other.

8. An intervertebral implant for being implanted between adjacent vertebrae, the intervertebral implant comprising:
- a generally elongate implant body extending along a longitudinal axis between first and second longitudinal ends positioned opposite one another, and an intermediate portion located between the first and second longitudinal ends;
- a lateral wall positioned in the intermediate portion and extending transverse to the longitudinal axis;
- a superior face of the implant body;
- an inferior face of the implant body;
- a first throughopening positioned in the intermediate portion and being at least partially defined by the lateral wall and a first interior surface, the first interior surface extending between a first opening in the superior face and a second opening in the inferior face, the first throughopening extending through the implant body and configured to receive fusion material therein;
- a second throughopening positioned in the intermediate portion and being at least partially defined by the lateral wall and a second interior surface, the second interior surface extending between a third opening in the superior face and a fourth opening in the inferior face, the second throughopening extending through the implant body and configured to receive fusion material therein;
- a plurality of protrusions extending from the first and second interior surfaces; and
- a plurality of teeth on the superior and inferior faces in the intermediate portion, the lateral wall at least partially separating the first and second throughopenings and having a length defining a common width of the first and second throughopenings;
- wherein the plurality of teeth comprise cortical teeth and central teeth, and
- wherein the cortical and central teeth have peaks with the central teeth peaks being sharper than the cortical teeth peaks.

9. An intervertebral implant for being implanted between adjacent vertebrae, the intervertebral implant comprising:
- a generally elongate implant body extending along a longitudinal axis between first and second longitudinal ends positioned opposite one another, and an intermediate portion located between the first and second longitudinal ends;
- a lateral wall positioned in the intermediate portion and extending transverse to the longitudinal axis;
- a superior face of the implant body;
- an inferior face of the implant body;
- a first throughopening positioned in the intermediate portion and being at least partially defined by the lateral wall and a first interior surface, the first interior surface extending between a first opening in the superior face and a second opening in the inferior face, the first throughopening extending through the implant body and configured to receive fusion material therein;
- a second throughopening positioned in the intermediate portion and being at least partially defined by the lateral wall and a second interior surface, the second interior surface extending between a third opening in the superior face and a fourth opening in the inferior face, the second throughopening extending through the implant body and configured to receive fusion material therein;
- a plurality of protrusions extending from the first and second interior surfaces; and
- a plurality of teeth on the superior and inferior faces in the intermediate portion,
- the lateral wall at least partially separating the first and second throughopenings and having a length defining a common width of the first and second throughopenings;
- wherein the plurality of teeth comprise cortical teeth and central teeth, and
- wherein each of the cortical teeth and central teeth include peaks with the central teeth have a greater spacing between adjacent peaks than the spacing between adjacent peaks of the cortical teeth.

10. An intervertebral implant for being implanted between adjacent vertebrae, the intervertebral implant comprising:
- a generally elongate implant body extending along a longitudinal axis between first and second longitudinal ends positioned opposite one another, and an intermediate portion located between the first and second longitudinal ends;
- a lateral wall positioned in the intermediate portion and extending transverse to the longitudinal axis;
- a superior face of the implant body;
- an inferior face of the implant body;
- a first throughopening positioned in the intermediate portion and being at least partially defined by the lateral wall and a first interior surface, the first interior surface extending between a first opening in the superior face and a second opening in the inferior face, the first throughopening extending through the implant body and configured to receive fusion material therein;
- a second throughopening positioned in the intermediate portion and being at least partially defined by the lateral wall and a second interior surface, the second interior surface extending between a third opening in the superior face and a fourth opening in the inferior face, the second throughopening extending through the implant body and configured to receive fusion material therein;
- a plurality of protrusions extending from the first and second interior surfaces; and
- a plurality of teeth on the superior and inferior faces in the intermediate portion,
- the lateral wall at least partially separating the first and second throughopenings and having a length defining a common width of the first and second throughopenings;
- wherein the plurality of teeth comprise cortical teeth and central teeth, and
- wherein the cortical teeth are arranged in a predetermined area on each of the superior and inferior faces in a generally arcuate configuration.

11. An intervertebral implant for being implanted between adjacent vertebrae, the intervertebral implant comprising:
- a generally elongate implant body extending along a longitudinal axis between first and second longitudinal ends positioned opposite one another, and an intermediate portion located between the first and second longitudinal ends;
- a lateral wall positioned in the intermediate portion and extending transverse to the longitudinal axis;
- a superior face of the implant body;
- an inferior face of the implant body;
- a first throughopening positioned in the intermediate portion and being at least partially defined by the lateral wall and a first interior surface, the first interior surface extending between a first opening in the superior face and a second opening in the inferior face, the first throughopening extending through the implant body and configured to receive fusion material therein;
a second throughopening positioned in the intermediate portion and being at least partially defined by the lateral wall and a second interior surface, the second interior surface extending between a third opening in the superior face and a fourth opening in the inferior face, the second throughopening extending through the implant body and configured to receive fusion material therein;
a plurality of protrusions extending from the first and second interior surfaces; and
a plurality of teeth on the superior and inferior faces in the intermediate portion,
the lateral wall at least partially separating the first and second throughopenings and having a length defining a common width of the first and second throughopenings;
wherein the plurality of teeth comprise cortical teeth and central teeth, and
wherein the cortical teeth are arranged in a first density per unit area and the central teeth are provided in a second density per unit area that is less than the first density.

* * * * *